(12) United States Patent
Neal et al.

(10) Patent No.: US 12,343,081 B2
(45) Date of Patent: Jul. 1, 2025

(54) OPTICAL ABERROMETER SYSTEMS FOR CUSTOMIZING INTRAOCULAR LENS

(71) Applicant: Wavefront Dynamics, Inc., Albuquerque, NM (US)

(72) Inventors: Daniel R. Neal, Albuquerque, NM (US); R. James Copland, Albuquerque, NM (US); Jeff Kolberg, Laguna Beach, CA (US)

(73) Assignee: WaveFront Dynamics, Inc., Albuquerque, NM (US)

( * ) Notice: Subject to any disclaimer, the term of this patent is extended or adjusted under 35 U.S.C. 154(b) by 627 days.

(21) Appl. No.: 17/830,279

(22) Filed: Jun. 1, 2022

(65) Prior Publication Data
US 2022/0369922 A1 Nov. 24, 2022

Related U.S. Application Data

(63) Continuation-in-part of application No. 17/325,168, filed on May 19, 2021, now Pat. No. 12,245,972.

(51) Int. Cl.
*A61B 3/10* (2006.01)
*A61B 3/14* (2006.01)
*A61F 9/008* (2006.01)

(52) U.S. Cl.
CPC .............. *A61B 3/1015* (2013.01); *A61B 3/14* (2013.01); *A61F 9/008* (2013.01)

(58) Field of Classification Search
CPC ......... A61B 3/1015; A61B 3/14; A61F 9/008; A61F 9/00834; A61F 2009/0087; A61F 2009/0088
See application file for complete search history.

(56) References Cited

U.S. PATENT DOCUMENTS

| 3,536,383 A | 10/1970 | Cornsweet |
| 4,287,410 A | 9/1981 | Crane |
| 4,373,787 A | 2/1983 | Crane |
| 4,834,528 A | 5/1989 | Howland |

(Continued)

FOREIGN PATENT DOCUMENTS

| WO | WO2004084719 | 7/2004 |
| WO | WO2004072709 | 8/2004 |
| WO | WO2012130818 A1 | 4/2012 |

OTHER PUBLICATIONS

Xin Wei, Larry Thibos "Design and validation of a scanning Shack Hartmann aberrometer for measurements over a wide field of view," Optics Express, Jan. 18, 2010, vol. 18, No. 2, , p. 1134-1143.

(Continued)

*Primary Examiner* — Jack Dinh
(74) *Attorney, Agent, or Firm* — Quinn IP Law

(57) ABSTRACT

A system for correcting vision in an eye that uses a premium, customized IOL, the system comprising: (1) optical aberrometer means for measuring wavefront aberrations of the eye; (2) computer means for designing a wavefront-customized correction profile for the IOL; (3) manufacturing means for creating a customized IOL with the wavefront-corrected profile; and (4) surgical means for implanting the customized IOL in the eye. Alternatively an uncorrected IOL is first implanted and aligned in the eye, followed by in-situ scanning a femtosecond laser spot across the implanted IOL to locally change an index of Refraction of the IOL material in-situ.

8 Claims, 10 Drawing Sheets

(56) References Cited

U.S. PATENT DOCUMENTS

| | | |
|---|---|---|
| 4,836,670 A | 6/1989 | Hutchinson |
| 5,430,505 A | 7/1995 | Katz |
| 5,430,509 A | 7/1995 | Kobayashi |
| 5,777,719 A | 7/1998 | Williams |
| 5,949,521 A | 9/1999 | Williams |
| 6,086,204 A | 7/2000 | Magnante |
| 6,095,651 A | 9/2000 | Williams |
| 6,499,843 B1 | 12/2002 | Cox |
| 6,511,180 B2 | 1/2003 | Guirao |
| 6,550,917 B1 | 4/2003 | Neal |
| 6,554,425 B1 | 4/2003 | Roffman |
| 6,634,750 B2 | 10/2003 | Neal |
| 6,830,712 B1 | 12/2004 | Roffman |
| 6,848,790 B1 | 2/2005 | Dick |
| 7,044,944 B2 | 5/2006 | Campin |
| 7,572,008 B2 | 8/2009 | Elvesjo |
| 7,699,467 B2 | 4/2010 | Dick |
| 7,963,652 B2 | 6/2011 | Vertegaal |
| 8,360,578 B2 | 1/2013 | Nummela |
| 8,678,591 B2 | 3/2014 | Zhou |
| 9,167,965 B2 | 10/2015 | Jaeken |
| 9,301,675 B2 | 4/2016 | Kiderman |
| 9,649,029 B2 | 5/2017 | Blixt |
| 9,918,873 B2 | 3/2018 | Woodley |
| 9,949,636 B2 | 4/2018 | Kersting |
| 9,999,348 B2 | 6/2018 | Gao |
| 10,080,493 B2 | 9/2018 | Reimer |
| 10,188,287 B2 | 1/2019 | Copland |
| 10,251,784 B2 | 4/2019 | Woodley |
| 10,278,576 B2 | 5/2019 | Hwang |
| 10,420,466 B2 | 9/2019 | Cornsweet |
| 10,166,731 B2 | 11/2019 | Grubbs |
| 10,463,248 B2 | 11/2019 | Cornsweet |
| 10,485,655 B2 | 11/2019 | Pinto |
| 10,579,141 B2 | 3/2020 | Aleem |
| 10,606,072 B2 | 3/2020 | Aleem |
| 10,694,938 B2 | 6/2020 | Janunts |
| 10,718,942 B2 | 7/2020 | Egea |
| 10,813,550 B2 | 10/2020 | Copland |
| 2004/0021826 A1 | 2/2004 | Sarver |
| 2011/0273669 A1 | 11/2011 | Arbitol |
| 2018/0003981 A1 | 1/2018 | Urey |
| 2018/0129041 A1 | 5/2018 | Aleem |
| 2018/0129279 A1 | 5/2018 | Melman |
| 2018/0207031 A1 | 7/2018 | Woodley |
| 2018/0249906 A1 | 9/2018 | Gramatikov |
| 2018/0344157 A1 | 12/2018 | Ng |
| 2019/0231590 A1 | 8/2019 | Woodley |
| 2020/0154996 A1 | 5/2020 | Blixt |

OTHER PUBLICATIONS

Blanton, US "Meta-analysis of six excimer laser platforms for safety and efficacy in myopic laser-assisted in situ keratomileusis," Ophthalmic Review vol. 8, Issue 1 Spring 2015.

Moussa "Visual aberrometric photic patient satisfaction LASIK w high resolution aberrometer," Opth-10-2489.

Zheleznyak, "First demonstration of human visual performance through refractive-index modified ophthalmic devices written in hydrogels," IOVS vol. 58(8) 1274-1274.

G. Gandara-Montano, "Optical bench testing of gradient-index Fresnel lenses written with femtosecond laser induced refractive index change," IOVS vol. 58(8), 1275-1275].

E. Manche, "Wavefront-optimized versus wavefront-guided LASIK: One-year results of a contralateral eye study," ASCRS 26 2018.

B. Alqattan, A.K. Yetisen, H Butt, "Direct Laser Writing of Nanophotonic Structures on Contact Lenses", ACS Nano 2018, 12, 5030-5040.

X. He, et al., Relative position of the central hole after EVO-ICL implantation for moderate to high myopia; BMC Ophthalmology (2020) 20:305.

Regular Iris Imaging System

Dark-Field Iris Imaging System

Multi-Zone Intra Ocular Lens (MZ-IOL), 30

OPTICAL ABERROMETER SYSTEMS FOR CUSTOMIZING INTRAOCULAR LENS

CROSS-REFERENCES TO RELATED APPLICATIONS

This application is related to co-pending application "Methods for Customizing Intraocular Lens Using an Optical Aberrometer", which was filed on the same day by Daniel R. Neal, R. James Copland and Jeff Kolberg, and which is incorporated herein by reference. This application is also a Continuation-In-Part (CIP) of U.S. Ser. No. 17/325,168, "System and Method for Customizing an Intraocular Lens Using a Wavefront Abberometer" by Daniel R. Neal, R. James Copland, Alan Blair, and Xifeng Xiao, filed May 5, 2021 which is also incorporated herein by reference.

FIELD OF THE INVENTION

The general field of the invention includes ophthalmology and optometry, and the use of specialized optical instruments (aberrometers) that use wavefront sensors for measuring on-axis (central vision) aberrations of an eye's optical properties Customized contact lenses can be made that correct for these measured aberrations.

BACKGROUND OF THE INVENTION

Intra-ocular lenses (IOLs) are used to replace an opaque or cloudy lens in the eye during cataract surgery. Increasingly, these lenses have been used to correct refractive error as well. A phakic IOL is used to correct refractive error in a patient while retaining the natural lens. The word "Phakic" refers to a situation where the patient's natural crystalline lens is left untouched during an operation (as opposed to cataract surgery, which removes the clouded lens). Phakic intra-ocular lenses (IOLs) are currently made by Staar Surgical, AMO, and Ophtec. The Staar phakic IOL is named "Visian ICL" and it is implanted between the iris and the crystalline lens. Visian ICL (Implanted Contact Lens) is made of soft collamer material that is manufactured by Staar. The most commonly used version only corrects spherical errors (sphere) but it is also available in a toric version for correcting astigmatism [U.S. Pat. No. 10,485,655]. The AMO phakic IOL is named "Veriseye" and it is implanted in the anterior chamber of the eye, in between the iris and the cornea. Veriseye is made of rigid PMMA plastic. The Ophtec phakic IOL is named "Artiflex" and it also is implanted in anterior chamber of the eye. It is available as sphere only or as a toric. Phakic IOLs are FDA-approved for refractive correction for people between the ages of 21 and 40 years old and for refractive errors between −6 D end −20 D.

IOLs have many advantages. Compared to traditional contact lenses, IOLs are permanently implanted so there is no daily routine of putting them in and taking them out. Compared to LASIK or PRK, IOLs can often be implanted in eyes that are not suitable for LASIK or PRK due to conditions such as thin corneas or extreme myopia that is outside the range that LASIK is able to treat. Sometimes a IOL can be placed in an eye that has extreme myopia to correct the majority of the refractive error and then LASIK corrects the residual error.

The disadvantage of IOLs is that generally the level of visual acuity that is achieved is not as good as what is routinely achieved with contact lenses or LASIK. According to Dr. Brian Boxer Wachler, writing on the website www.AllAboutVision.com, "In a study of 3-year outcomes of the FDA clinical trial of the Verisyse lens, 84% of patients achieved uncorrected vision of 20/40 or better, which is the legal limit for driving without prescription eyewear in most states. And, 31% achieved uncorrected vision of 20/20 or better. In FDA trials of the posterior chamber Visian ICL, 81% of patients achieved uncorrected visual acuity of 20/40 or better. Forty-one % attained uncorrected vision of 20/20 or better." By comparison for LASIK, over 90% of patients attain uncorrected vision of 20/20 or better.

Part of the difference is because IOLs are being used with patients that have more severe visual problems than a typical LASIK patient that may be only having a few diopters of refractive error being corrected. Also, part of the modern success of LASIK has been the application of wavefront measurement in planning and in post-surgical evaluations that have resulted in steady improvements in the LASIK treatments. Also, the surgeons can target precise treatment zones for LASIK by use of iris registration eye tracking. By contrast, the application of wavefront measurements to improving phakic IOLs has been less intense. And there remains a difficulty that surgeons do not have good control or ability to predict exactly where a IOL will end up in the eye after a surgery.

The goal of the inventions described in this disclosure is to bring wavefront technology into IOL planning and evaluation steps to improve visual outcomes. IOLs present various technical differences and difficulties that require novel ideas to enable effective systems and procedures. These include being able to measure the eye and predict the final IOL's position. Horizontal and vertical positioning is one area of difficulty. Also, the precise location of the IOL along the optical axis of the eye is of concern. Another area of difficulty is that IOLs are more frequently being used for patients that have keratoconus (progressive thinning of the cornea). Theoretically, a customized IOL can be machined to correct aberrations from the cornea once those have been measured with a wavefront aberrometer. But the customized shape typically would only achieve 20/20 vision if the IOL were positioned within 0.2 mm of the optical axis and rotated to within 5 degrees of the ideal. Increased displacements from the ideal position result in a reduction in visual acuity that is more pronounced as the displacement increases.

Visian phakic ICLs made by Staar Surgical have a unique feature, which is small, central hole (e.g. U.S. Pat. No. 10,485,655). Early versions of Visian ICL's did not have such a hole and sometimes patients would develop cataracts in response to the implant. Initially, the cause was believed to be contact between the crystalline lens and the IOL. However, it was found that a central hole actually prevented cataract formation, probably because it enabled fluid exchange. The hole is small, so it has minimal effect on the visual acuity of the patient. The hole is difficult to see by someone who is looking at the IOL, but it can be detected under slit lamp examination. For adapting wavefront technology to Visian ICL lenses, the hole may serve as a good indicator of IOL position after implantation.

Wavefront aberrometers have been effectively used to measure the ocular aberrations of the human eye. A small spot of light is projected onto the cornea and the scattered light is collected by the lens and cornea and imaged onto a wavefront sensor (Shack-Hartmann, pyramid, interferometer, etc.) The sensor measures the wavefront of the light to find optical properties of the eye [U.S. Pat. Nos. 6,550,917, RE42,782 D, 7,699,467, 6,848,790, WO 99/27334, WO 00/19385, WO 00/08415, U.S. Pat. Nos. 6,634,750, 5,430,509, 6,086,204, 6,511,180, 6,095,651, 6,086,204, and 5,777, 719]. The measurement can be analyzed in terms of standard Zernike polynomials and provides information about the ocular optical system. Wavefront based refraction has been shown to closely match the refraction measured with subjective methods [E. Manche, "Wavefront-optimized versus wavefront-guided LASIK: One-year results of a contralateral eye study," ASCRS 26 2018]. The refraction is derived primarily from the low order aberration terms while higher order terms describe additional aberrations of the eye. These higher-order aberrations can affect vision as well as the base refraction.

Measured wavefront aberrations have been used as a guide for surgical correction of a patient's vision. Laser refractive surgery has developed systems and methods for using the wavefront information to either optimize optical structures [U.S. Pat. No. 7,044,944] or directly guide the surgery [U.S. Pat. Nos. 5,949,521, 6,095,651]. Specialty instruments have been developed that incorporate both wavefront aberrometry and corneal topography in a single instrument, which allows for co-aligned measurement of the total aberrations and anterior cornea along a single (and known) fixation axis. This provides information needed for guiding the surgery, and for planning a laser treatment that incorporates known reflection and beam footprint calibrations [Clinical and patient reported outcomes after wavefront guided LASIK for myopia using a high-definition. Hartmann Shack Aberrometer." C. Kraff, R. Maloney, and S. Coleman, ASCRS 23_2018.]. The wavefront-guided treatment methodology has been shown to be effective at producing excellent patient outcomes using laser refractive surgery [S. Moussa et al. "Visual, aberrometric, photic phenomena, and patient satisfaction after myopic wavefront-guided LASIK using a high-resolution aberrometer," Clinical Ophthalmology 2016:10 2849-2496; C. Blanton, "Meta-analysis of six excimer laser platforms of safety and efficacy in myopic Laser-Assisted in situ keratomileusis, US Ophthalmic, Review Vol 8 (1), Spring 2015].

The wavefront-guided approach has also been applied to other treatment modalities [U.S. Pat. Nos. 5,777,719, 6,086, 204], including contact lenses [U.S. Pat. Nos. 6,499,843, 6,554,425, 6,830,712, and WO 04072709A], with some success. However, these techniques have not been used in wide clinical practice, partially due to the instability of the contact lens on the eye. This is difficult to overcome because the comfort of the contact lens depends to some extent on the fact that it moves on the eye, spreading the tear film and providing oxygen to the cornea.

Some other technologies exist that provide correction for optical error of the eye and that do not move appreciably. The World Health Organization estimates that 20 million IOLs were implanted worldwide in 2010, and they project 32 million will be implanted annually by 2020. The vast majority of IOLs are simple monofocal designs, but increasingly premium IOLs are being developed that incorporate wavefront adjustments into their design. The IOL may be implanted in the capsular bag after removal of the natural (presumably cataractous) lens, or implanted in the sulcus, just behind the iris [U.S. Pat. No. 10,485,655], or even "clipped" to the iris itself.

New techniques can modify the refractive/diffractive characteristics of an IOL or ICL in vivo by changing the index of refraction with a small spot, scanning, pulsed laser beam [L. Zheleznyak, "First demonstration of human visual performance through refractive-index modified ophthalmic devices written in hydrogels," IOVS Vol. 58(8) 1274-1274, G. Gandara-Montano, "Optical bench testing of gradient-index Fresnel lenses written with femtosecond laser induced refractive index change," IOVS Vol. 58(8), 1275-1275]. The beam in the eye must be precisely positioned and controlled and that requires accurate measurement to direct and monitor beam delivery. The process of writing a desired optical pattern on an IOL can take tens of seconds. During that time, the IOL may move in the eye even if the eye has been applanated by external means. A method is needed to track the position and tip/tilt of the IOL in the eye in real-time during the procedure.

A number of optical techniques have been developed to measure structures in the eye; including wavefront aberrometry, corneal topography, ultrasound, and optical coherence tomography (OCT). However, these techniques are usually aimed at a more general diagnosis of the eye, and they lack the combination of accuracy, dynamic range and speed to actively control surgical procedures. All references cited herein are incorporated herein by reference in their entirety. Against this background, the following invention was developed.

SUMMARY OF THE INVENTION

The present invention comprises systems and methods for correcting vision in an eye that uses a customized IOL, pseudophakic IOL, or phakic IOL, the system comprising: (1) means for measuring one or more wavefront aberrations of the eye; (2) means for designing a wavefront-customized correction profile for an Intraocular Lens (IOL); (3) means for creating a customized IOL with the customized correction profile; and (4) means for implanting the customized IOL in the eye. Alternatively, an uncorrected IOL is first implanted and aligned in the eye, followed by in-situ scanning a femtosecond laser spot across the implanted IOL to locally change in-situ the Index of Refraction of the IOL material and create an in-situ customized IOL.

DETAILED DESCRIPTION OF THE INVENTION

In this application, use of the acronym "IOL" is broadly construed to include both phakic IOLs, pseudophakic IOLs, and non-phakic IOLs.

Figure 1:
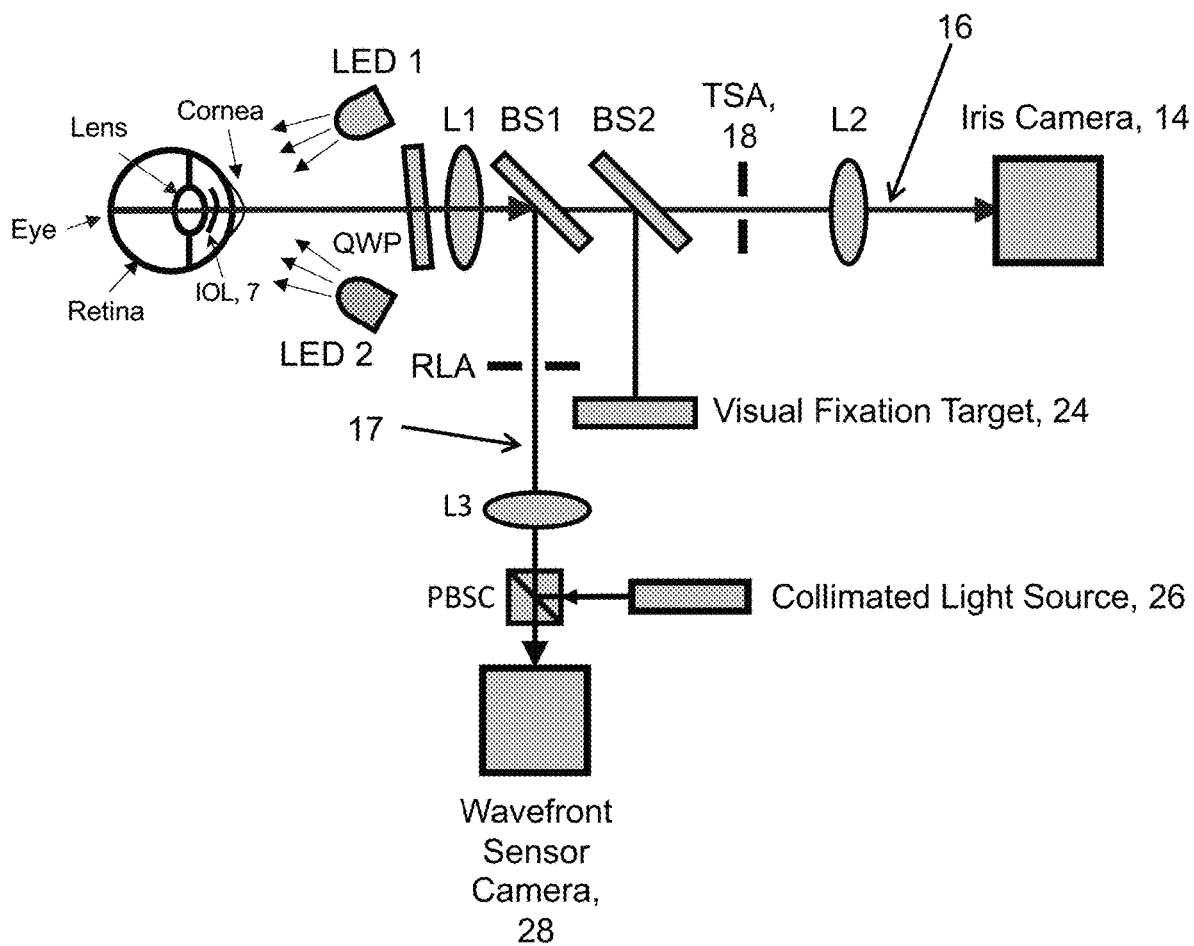
FIG. 1 refers to an optical schematic layout of a first example of an ophthalmic wavefront aberrometer, according to the present invention.

FIG. 1 shows an optical schematic of a first example of an ophthalmic wavefront aberrometer. The aberrometer has 2 optical paths disposed at 90 degrees to each other, including: a regular iris imaging path 16 and a wavefront imaging path 17. The first step of measuring a patient's eye is that the instrument operator aligns the optical instrument to the patient's eye. He/she is aided in this task by the visual image that is generated by iris camera 14. Once the instrument is aligned, the patient is instructed to look at the internal visual target 24. The target typically simulates a distant scene. For example, a hot air balloon hovering over a distant horizon. While the patient looks at the target 24, the collimated light source 26 emits a narrow beam of light. The light in the beam can be S-polarized and it is barely noticed by the patient because (preferably) it is infrared light with a wavelength of 840 nm. Other wavelengths can be used, as needed. The light reflects off the hypoteneuse of the Polarizing Beam Splitting Cube (PBSC). The light travels through the rear len L2, reflects off beamsplitter BS1, travels through front lens L1, then through the quarter wave plate (QWP). The QWP converts the light to circular polarization. Then, the probe light travels into the eye as a narrow beam 16 along the optical axis of the instrument. The cornea and internal crystalline lens focus the beam onto the eye's retina. A small fraction of the light scatters off the retina in all directions. About 0.5% percent of the light goes back toward the cornea and creates an outgoing beam that is same diameter as the iris. For an emmetrope, the outgoing beam is nearly collimated. For a myope, the beam converges slightly as it leaves the cornea. For a hyperope, the beam diverges.

Next, the light beam passes through the QWP and is converted to P-polarization. The light travels through L1, reflects off BS1, through 12 and reaches the PBSC. Since the light beam has been converted to P-polarization, it transmits through the PBSC cube, it then reaches the wavefront sensor camera 28. A computer analyzes the images taken by the wavefront sensor 28 and then calculates the patient's refraction and aberrations.

Figure 2:
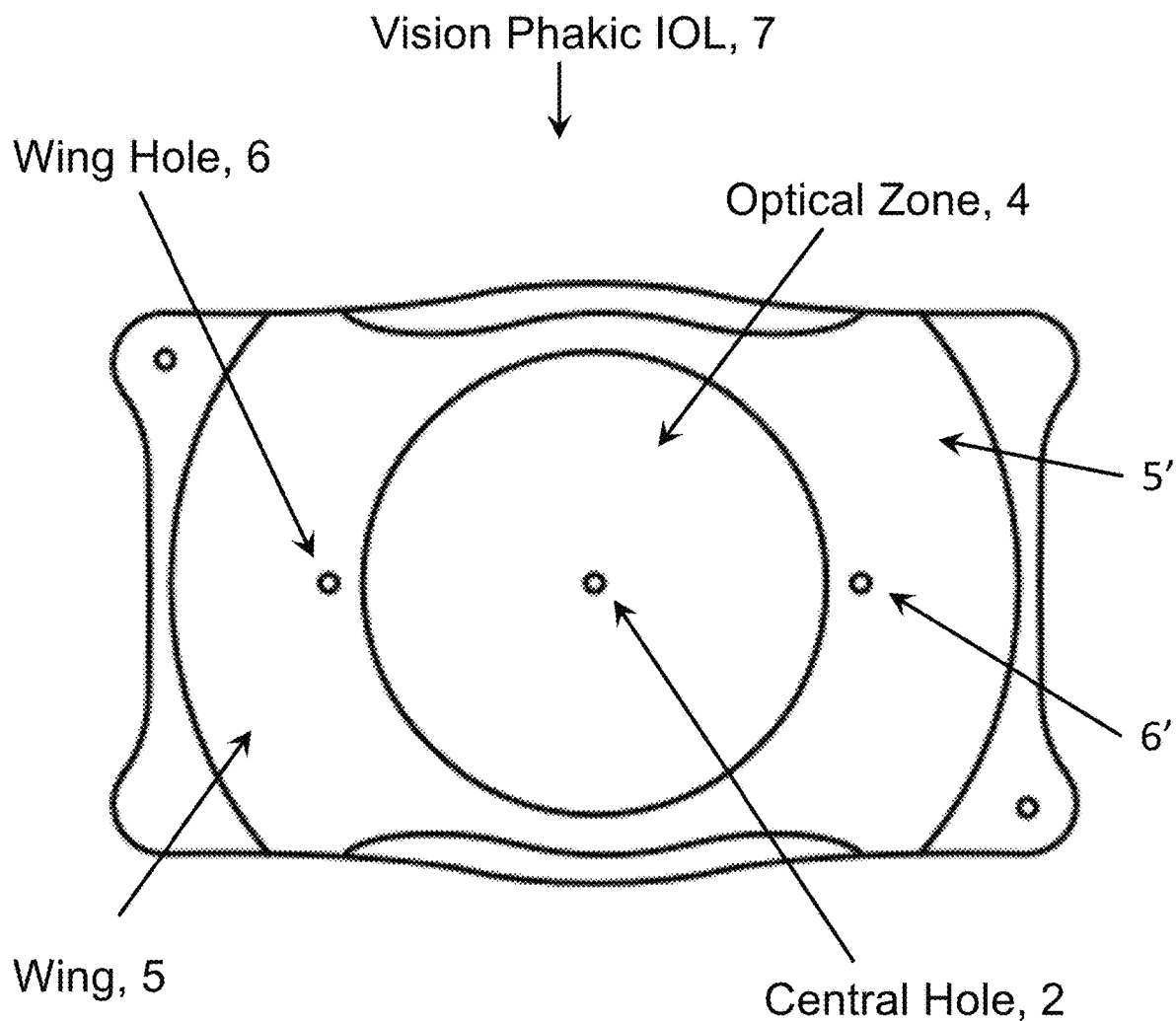
FIG. 2 is a plan view of a first example of an intraocular lens (IOL).

FIG. 2 shows a plan view of an example of a Visian ICL (phakic IOL 7) that has a central hole 2. The large central circle represents the optical zone 4 of the IOL. The rectangular portions are the wings 5, 5' that fit into the space (posterior chamber) in between the iris and the natural lens of the eye. The central hole 2 allows fluid exchange across the perforated IOL structure that prevents the perforated IOL from inducing cataract formation. Additional thru-holes 6, 6' can be added to further perforate the IOL (up to a point where visual acuity is negatively affected).

Figure 3:
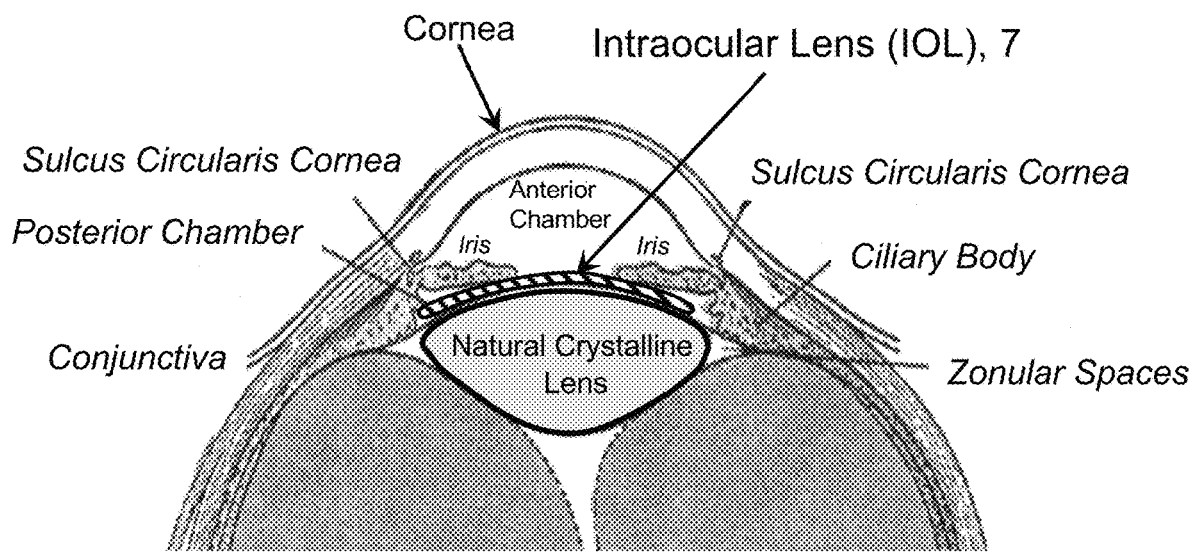
FIG. 3 shows a cross-section view showing a human eye's anatomy.

FIG. 3 shows a cross-section view of the anatomy of a human eye. The phakic IOL 7 usually sits either just behind the iris in the Posterior Chamber, and is constrained by the ciliary body. It can also sit in-between the cornea and iris (e.g., in an Anterior Chamber).

As described in the background section above, the Visian phakic ICL 7 has a central hole (aperture) 2 that could serve as an indicator of the ICL's XY position when imaged. Alternatively, a fiducial or other location mark could be placed on the phakic ICL to help identify its angular position in the eye. One embodiment of the instrument could measure the wavefront of the eye and nearly simultaneously find the position of the ICL using its central hole as a landmark. A second embodiment of a useful measurement instrument is a combined aberrometer/topographer/imager. In a third embodiment, this could have additional light sources that come in from the side to provide scattering from the edges of the hole. In a fourth embodiment, this device could also be modified to include a "dark field" imaging path.

Figure 4:
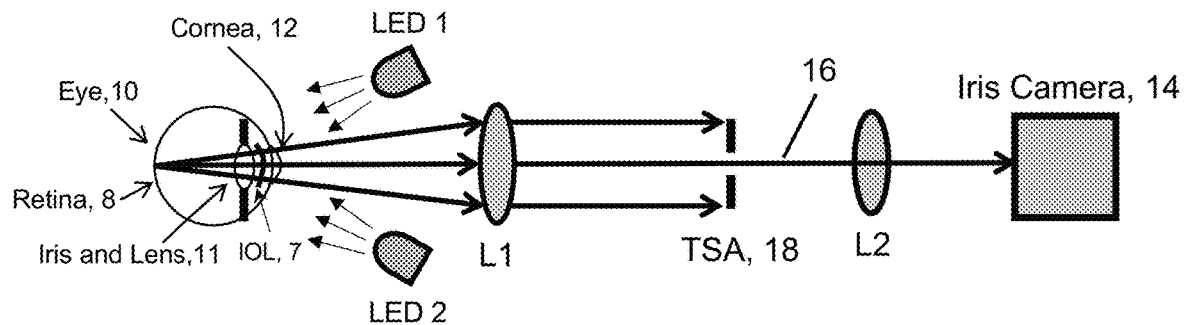
FIG. 4 shows an optical schematic layout of a second example of an ophthalmic wavefront aberrometer, according to the present invention.

FIG. 4 shows an optical schematic layout of a second example of an ophthalmic wavefront aberrometer, according to the present invention. This system is used for making a regular image, which houses an aperture labeled TSA (Telecentric Stop Aperture), 18. It can be simply a hole (aperature) of about 3 mm diameter in a solid disc. Lenses L1 and L2 are separated by a distance that equals the sum of their focal lengths. The TSA stop is located one focal length away from both lenses L1 and L2. This is a conventional telescopic regular imaging setup, and the image of the eye that forms on the iris camera 14 is a normal image.

Figure 5:
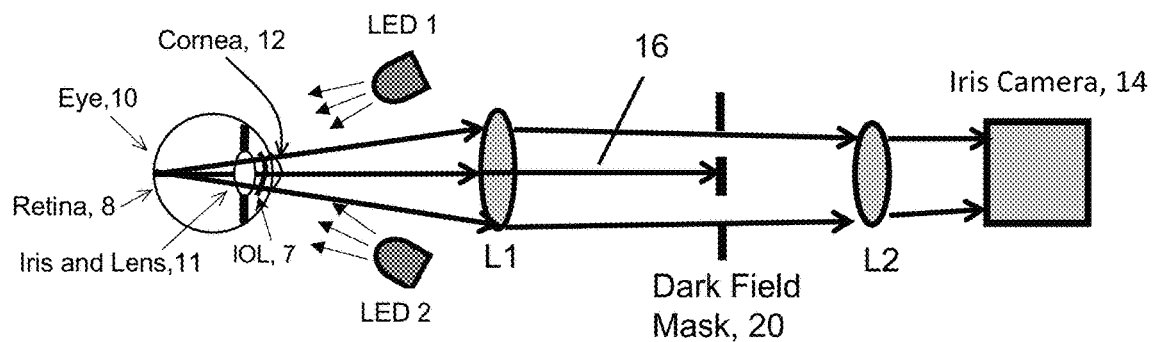
FIG. 5 shows an optical schematic layout of a third example of an ophthalmic wavefront aberrometer with a Dark-Field mask, according to the present invention.

Dark field imaging is a well-known optical technology to those skilled in the art. However, its use for imaging eye structures and features of optical structures implanted in eyes is novel. FIG. 5 shows an optical schematic layout of a third example of an ophthalmic wavefront aberrometer with a Dark-Field mask, according to the present invention. The lower figure FIG. 5, used for making a dark field image, is the same as the embodiment in upper figure FIG. 4, except that the TSA optic 18 has been replaced by a dark field mask (DFM) optic 20. A practical system could switch between the two different configurations by using a solenoid (not shown) to physically exchange the two items with a third optic, such as a Spatial Light Modulator (SLM); a small motor; rotation disk; or other means for repeatedly modulating the light travelling down the optical path.

Figure 6:
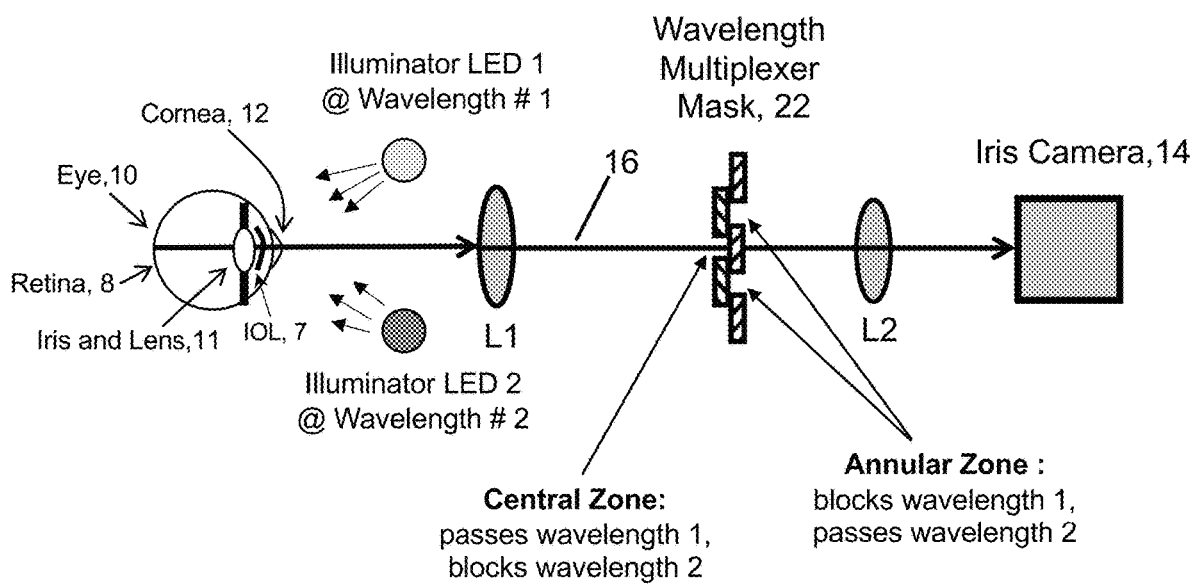
FIG. 6 shows an optical schematic layout of a fourth example of an ophthalmic wavefront aberrometer with a first switchable imager, according to the present invention.

In another embodiment of a measurement system, instead of physically moving a TSA optic 18 and/or DFM optic 20 back and forth along the optical path 16, it is possible to use a stationary Wavelength Multiplexed Mask (WMM) optic 22. FIG. 6 illustrates a first example of such a Switchable Imager system. In the Switchable Image embodiment of the optical system, the wavelength multiplexed mask (WMM) 22 can have a clear central hole surrounded by an annular region that blocks one selected wavelength #1 and passes a different wavelength #2. In this system, one would get a regular image in both optical setups, however one would like to have the edges enhanced. A software subtraction of two sequential images, for example, could be used to make a single dark field image.

In another embodiment, the system of FIG. 6 is modified by using a pair of individually controlled LED illumination sources (LED1 & LED2) emitting the same, or two different, wavelengths in FIG. 6, by switching sources On/Off between LED1 and LED2 only one side of the fiducial mark on the IOL would be illuminated. This will have the effect of enhancing the mark's shadows to make the fiducial feature more evident. Also, the LEDs could be alternatively switched On/Off on alternating frames of the iris camera 14 using active software control means.

As an example of a device made according to FIG. 1 the iDesign™ measurement instrument [Johnson & Johnson, 2012] comprises both a wavefront imaging path and a regular iris imaging path. The regular image path comprises a 4 F telecentric configuration using two lenses L1 and 12. Disposed in-between the two lenses L1 and L2 is a 3 mm diameter aperture in the TSA optic that serves as a telecentric stop that allows only rays to reach the iris camera 14 if they enter the instrument traveling nearly parallel to the optical axis 16 of the instrument. However, the rounded edge of the central aperture in the phakic IOL will tend to scatter light in many directions not parallel to the instrument s optical axis. The telecentric stop can be replaced with a DFM aperture that has a central obscuration. Such a device is called a "dark field mask" and it is useful to preferentially image the edges of objects, particularly if they have been illuminated by light coming in from the side. An improved instrument that uses iDesign™ technology can be constructed so a small motor switches the system between a conventional TSA telecentric stop and a DFM dark field mask. That would enable a multi-functional, combined instrument: (1) to serve as a corneal topographer, (2) to collect regular iris images, and (3) to find the central hole or other location feature/fiducial marks in an IOL.

Figure 7:
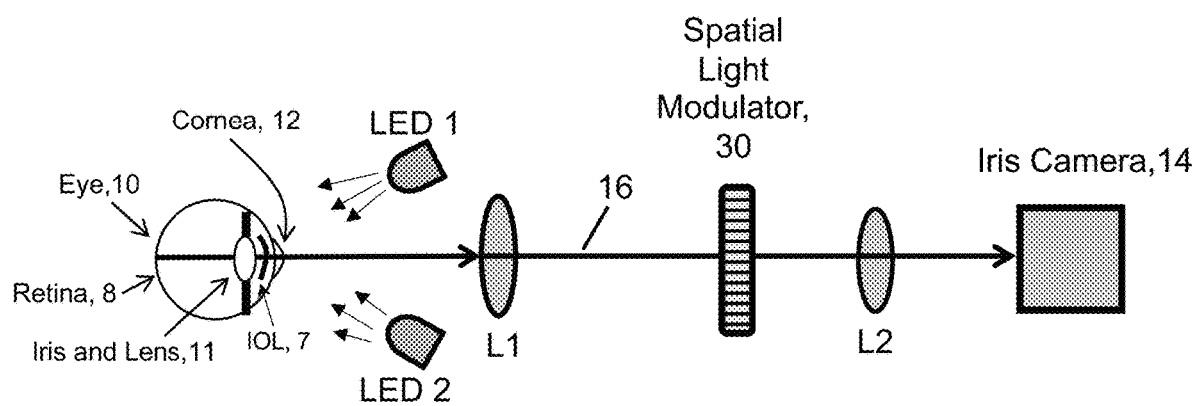
FIG. 7 shows an optical schematic layout of a fifth example of an ophthalmic wavefront aberrometer with a second switchable imager, according to the present invention.

FIG. 7 shows an optical schematic layout of a fifth example of an ophthalmic wavefront aberrometer with a second switchable imager, according to the present invention. Here, an alternate method of switching physical stops is to place a spatial light modulator (SIM) 30 at the location of the telecentric stop. For instance, a spatial light modulator can have a grid of N×N different hexagonal (or square or triangular) regions that can be rapidly turned on and off in transmission mode, enabling a variety of edge detection and optical processing techniques. In one embodiment, the number of hexagons is N=32.

Recently, femtosecond (FS) lasers have been developed that can change the index of refraction of plastic-like materials by focusing pulsed FS laser energy on a small area and then repeatedly scanning adjacent spots on the plastic to heat and change the optical properties of the small area. Such FS lasers can be used to modify the optical wavefront of IOLs in vivo. Guidance for actively controlling the FS laser spot can be provided by making measurements of the image's wavefront, it is also necessary to know the XYZ location of the plastic IOL material. The central hole in the Visian phakic ICL provides a convenient landmark that can be found, and hence provide the necessary XYZ fiducial location. Additional locations away from the central hole can then be found using Purkinje reflections. A central hole, or other location feature(s), including additional holes, can be added to any other manufacturer's IOL plastic designs to enable this optical enhancement technique.

Convenient methods of locating the XYZ location of the hole (or other location feature) in a IOL can include using split-prism range finders (such as are used in single lens reflex (SLR) cameras), OCT systems, stereo cameras, bi-cell detectors, or numerous other methodologies.

Another option is to use the femtosecond laser to create fiducial marks on the IOL that can be used for guiding and controlling the motion of a following laser pulse. Such marks can be either shallow spots that scatter light coherently, or deeper pits that scatter light incoherently. Or, they can be created to have diffractive structures, such as regularly spaced holes or lines that scatter light preferentially more strongly for certain incident angles and color combinations. Such a diffractively coded system can be created so a color camera effectively "sees" distance as color variations across an image.

In some cases, a doctor will implant a IOL that has tone marks to guide implantation relative to the degree of astigmatism in a patient's eye. Such marks can also be used with a system that creates a customized wavefront pattern on a IOL via a scanning femtosecond laser.

Typically, the manufacturer has a process of machining their IOL that can control the amount of sphere and cylinder errors and create any desired wavefront pattern. Measurement of a patient's wavefront pattern, that is made before a surgery, can be used to make an ideal wavefront-enhanced customized IOL. However, with their existing surgical procedures, currently manufactures are unable to take advantage of the potential improvements possible with customized wavefront patterns because of low predictability of where an implanted IOL will end up, both in XV position and in rotation, after implantation.

The outer haptic parts (e.g., wings) of a IOL generally extend over to the ciliary body that suspends the lens in the eye. The size and shape of the interstitial space in the Posterior Chamber between the ins and the ciliary body determine the final position of the IOL. Currently no clinically reliable means have been found to measure and characterize these interstitial spaces before the implantation of the ICL. Techniques that are being considered include, (a) using long wavelength Optical Coherence Tomography (OCT) through the iris, and (b) using long wavelength OCT through the sclera. Other techniques can utilize ultrasound and Magnetic Resonance Imaging (MRI) machines. The same techniques potentially may be used with implanted IOLs to learn more about the mechanism(s) that determine where an IOL finally ends up.

Another area that could use improvement with the current use of IOLs is that visual acuities reach 20/20 in only about 50% of procedures. This seems to be slightly lower than is achieved with typical monofocal IOL surgeries. Application of customized wavefront techniques would likely result in IOLs achieving better outcomes than typical IOL surgeries.

One embodiment of an optical system for correcting a person's vision can comprise:
 (a) optical aberrometer means for measuring wavefront aberrations of an eye;
 (b) computational means for designing a wavefront-customized correction profile that corrects a shape of an IOL to account for said measured aberrations:
 (c) manufacturing means for creating a customized IOL with the wavefront-customized correction profile, and
 (d) surgical means for implanting the customized IOL in the eye.

The manufacturing means for creating the customized IOL can comprise a numerically-controlled precision lathe with a numerically-controlled, fast, active Z-axis positioning driver. The manufacturing means for creating the customized IOL can comprise a pulsed laser. The optical aberrometer means can comprise both a wavefront imaging path and a regular image path. The optical aberrometer means can comprise a telecentric stop disposed in a regular image path and located one focal length away from both a front lens L1 and a rear lens L2 with both lens being disposed on the regular image path. The telecentric stop can comprise a central obscuration optic that can act as a "dark field mask". The optical aberrometer means can comprise a motor that physically switches the system from a telecentric stop optic to a dark field mask optic, as often as needed. The optical aberrometer means can comprise a spatial light modulator disposed on a regular image path, and located one focal length away from both a front lenses L1 and a rear lens L2, wherein both lenses are disposed along the regular image path.

The spatial light modulator can comprise a Wavelength Multiplexed Mask (WMM) that is configured for: (a) passing a first LED wavelength and blocking a second LED wavelength through a central zone of the mask, and simultaneously (b) blocking the first LED wavelength and passing the second LED wavelength through an annular zone of the mask; wherein the first wavelength is different than the second wavelength. The optical aberrometer means can comprise a first illumination LED Source and a second illumination LED Source, and the optical aberrometer means can further comprise switching means for switching on/off the first illumination LED out of phase with the second LED; thereby allowing a regular image to be formed when the first illumination LED is ON and the second illumination LED is OFF; and conversely, thereby allowing a dark field image to be formed when the first illumination LED is OFF and second illumination LED is ON. The manufacturing means can further comprise femtosecond laser means for creating one or more fiducial marks on a IOL that can be used for guiding a path of a following laser pulse, wherein said fiducial marks can be either spots that reflect light coherently or pits that scatter light incoherently.

The manufacturing means can further comprise femtosecond laser means for creating one or more diffractive fiducial features comprising regularly spaced holes or lines that scatter light preferentially more strongly at certain incident angles and color combinations. The optical aberrometer means can comprise a spatial light modulator (SLM) comprising a grid of N×N different hexagonal or square or triangular regions whose transmission can be controllably turned on and off, thereby enabling a variety of edge detection and optical processing techniques to be performed. The optical aberrometer means can comprise solenoid means for switching between a TSA optic, a dark field mask, a wavelength multiplexer mask, and a Spatial Light Modulator along an imaging path. The optical aberrometer means can comprise a motor for rotating a disk that repeatedly modulates light travelling down an imaging path of the optical means.

The optical aberrometer means can comprise a wavelength multiplexed mask (WMM) that has a clear central hole surrounded by an annular region that blocks one selected wavelength of illumination light and passes a different wavelength. The optical aberrometer means can comprise a first illumination LED Source and a second illumination LED Source; and can further comprise camera frame switching means for alternatively switching on/off alternate frames of an ins camera using software control means. The optical aberrometer means can comprise locating means for locating a XYZ location of a central hole or other fiducial mark in an IOL; wherein said locating means can comprise an optical system selected from the group consisting of a split-prism range finder, OCT system, stereo cameras, and one or more bi-cell defectors, and combinations thereof. The customized IOL can comprise one or more fiducial marks that comprise diffractive structures comprising regularly spaced apart holes or lines that scatter light preferentially more strongly at certain incident angles and color combinations; wherein a color camera can effectively "see" distance as color variations across a diffractively-coded image.

In other embodiments, IOLs may also be customized after implantation to provide improved vision. It may be advantageous to customize these IOLs in-situ after implantation and healing so that the lens is positioned at a relatively stable location in the eye. Several embodiments are possible for customizing IOLs in the eye. Either through the use of a femtosecond laser or through the use of a lens made of a special material that expands (swells non-uniformly) under the influence of external radiation (such as UV light).

Figure 8:
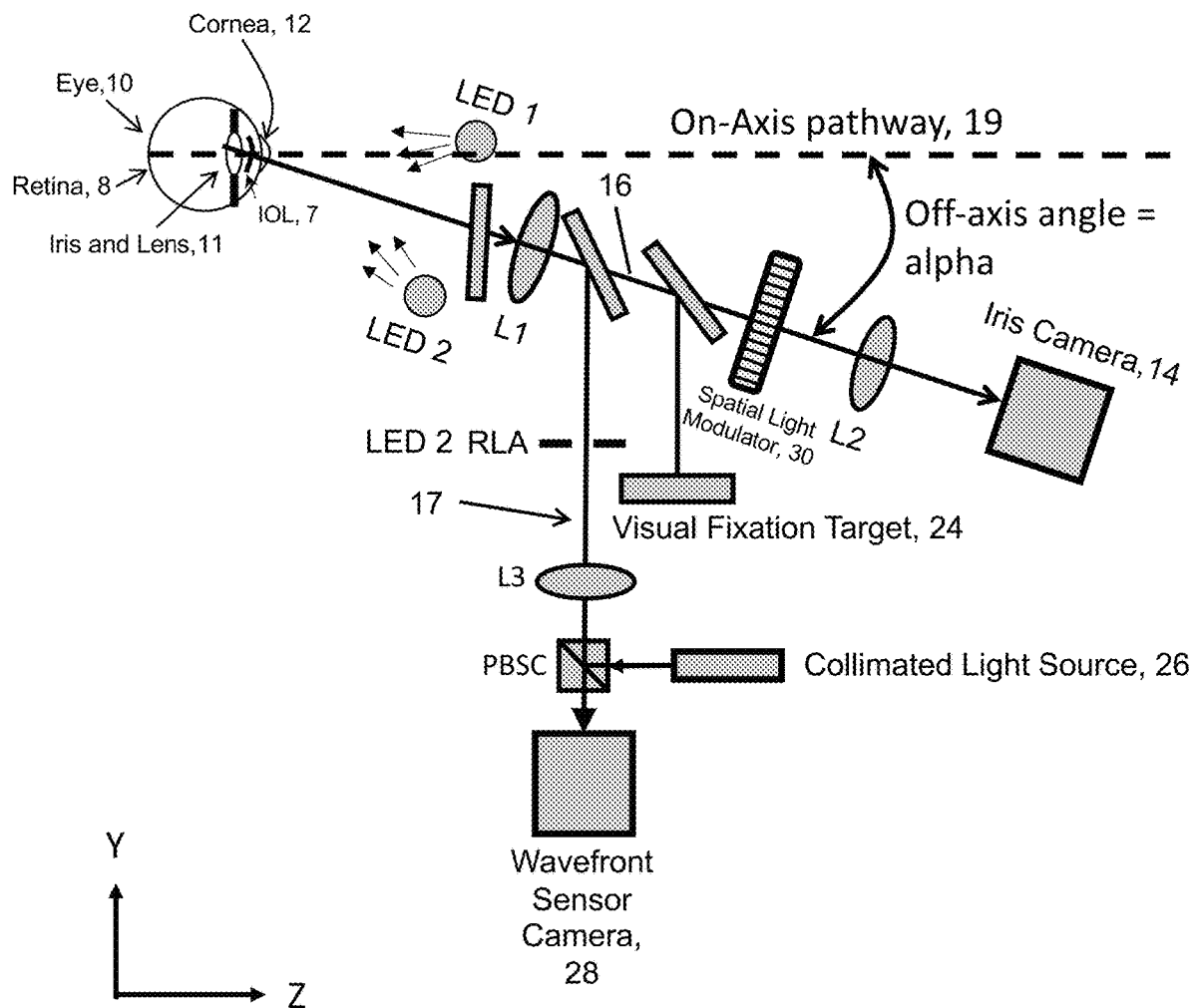
FIG. 8 shows an optical schematic layout of of a first example of an off-axis iris imaging system, combined with an optical aberrometer according to the present invention.

FIG. 8 shows a first alternate embodiment where the angle (alpha) between the iris imaging camera pathway 16 and the optical axis of the patent's eye can be different than a coventional On-Axis angle (where alpha=0 degrees). For example, the angle (alpha) can be continuously adjusted in-between +/−45 degrees. FIG. 8 shows a specific example of an off-axis angle "alpha"=−20 degrees. Adjusting the alpha angle in this way can enhance the system's ability to detect edges and fiducial artifacts, especially when combined with individualized control of illumination sources LED 1 and LED 2. Off-axis refractions of, for example, a patient with macular degeneration, can also be easily performed using this variation in the optical aberrometer design. In this first alternate embodiment, the wavefront sensor pathway 17 is positioned vertically (parallel to the Y-axis in this Figure), so that the complementary angle (not labelled) between the wavefront sensor pathway is equal to 70 degrees. Related to this first alternate embodiment, an innovative IOL can have two or three different radial zones, where a central/core zone (centered on R=0) optimized for on-axis refraction, while a different radial annulus (e.g., 1 or 2 or more different annular zones) that has a visual acuity is optimized for an off-axis refraction.

Figure 9:
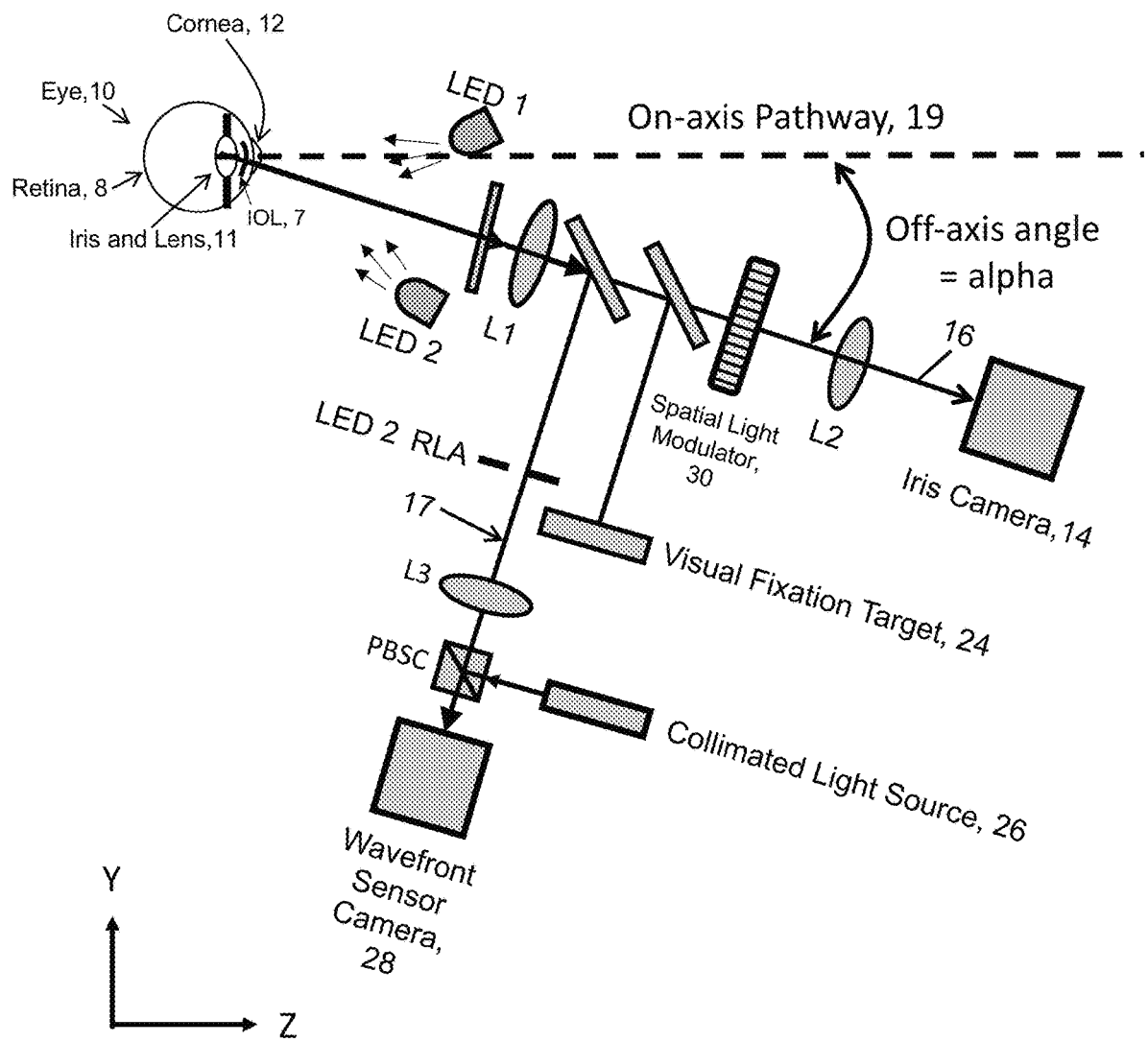
FIG. 9 shows an optical schematic layout of of a second example of an off-axis iris imaging system combined with an optical aberrometer, according to the present invention.

FIG. 9 shows a second alternate embodiment where the angle (alpha) between the iris imaging camera pathway 16 and the optical axis of the patent's eye can be different than a coventional On-Axis angle (=0 degrees). For example, the angle (alpha) can be continuously adjusted in-between +/−45 degrees. FIG. 9 shows a specific example of an off-axis probe beam angle "alpha"=−20 degrees. Adjusting the alpha angle in this way can enhance the system's ability to detect edges and fiducial artifacts, especially when combined with individualized control of illumination sources LED 1 and LED 2. Off-axis refractions of, for example a patient with macular degeneration can also be easily performed using this variation in the optical aberrometer design. In this second alternate embodiment, the wavefront sensor pathway 17 is positioned at 90 degrees to the iris imaging pathway 16. Related to this second alternate embodiment, an innovative IOL can have two or three different radial zones (i.e., MultiZone IOL), where a central/core zone (centered on R=0) optimized for on-axis refraction, while a different radial annulus (e.g., 1 or 2 or more different annular zones) has a visual acuity that is optimized for each off-axis refraction (which can be measured at a standardized off-axis angle, alpha).

Figure 10:
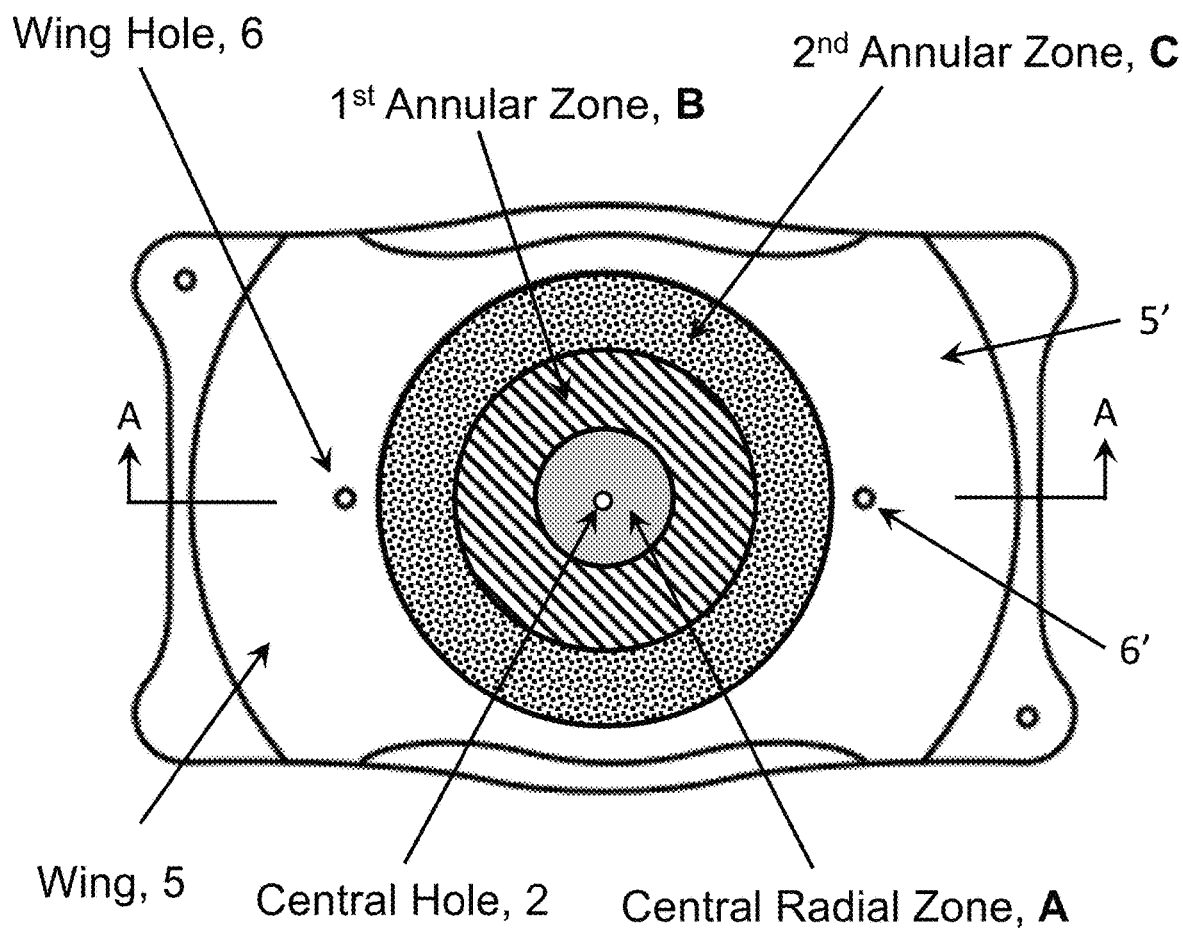
FIG. 10 shows a plan view of a first example of a multi-zone IOL, according to the present invention.

FIG. 10 shows a schematic plan view of a first example of a multi-zone IOL 30 (MZ-IOL), according to the present invention. Here, a Visian ICL, which has a small central hole 2, has a 3-D shape that has been modified according to a Multi-Zone method. In this example, the MZ-IOL 30 comprises three adjacent radial zones: a central radial zone, A; a first (intermediate) annular zone, B; and a second (outermost) Annular Zone, C. These three radial zones (A, B, C) correspond uniquely to three different angles of incidence (alpha) of the aberrometer probe beam 16 relative to the optical axis 19 of the patent's eye (see FIG. 12 for definitions). FIG. 1 shows an example of an first aberrometer setup where the probe beam angle, alpha, =0 degrees meaning that the probe beam 16 is parallel to, and coincides with, the optical axis 19 of the patient's eye. FIG. 8 shows an example of an second aberrometer setup where the angle, alpha=−20 degrees; meaning that the probe beam 16 is off-axis to (i.e., rotated down or to the side) relative to the optical axis 19 of the patient's eye. This setup in FIG. 8 corresponds, for example, to the 1st (intermediate) annular zone, B. A third setup (such as shown in FIG. 8 or 9) is not shown for brevity, but would be very similar to FIG. 8 or 9, and would have an even larger off-axis refraction angle, for example, alpha=−40 degrees, which corresponds to the $2^{nd}$ (outermost) annual zone, C.

Figure 11:
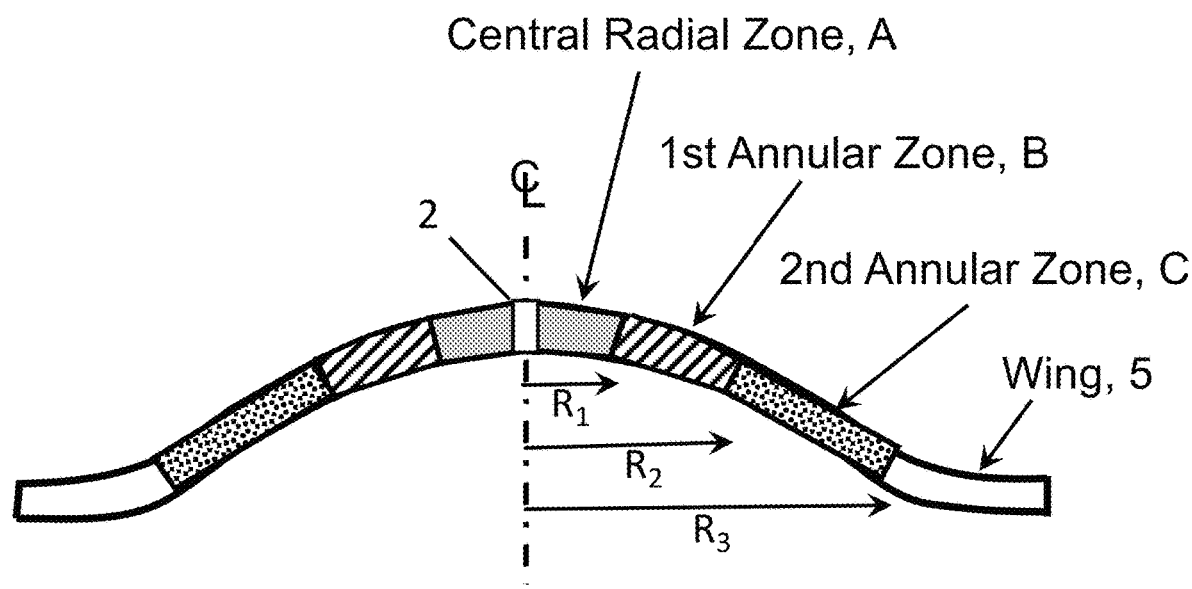
FIG. 11 shows a cross-sectional view of the first example of a multi-zone IOL, according to the present invention.

FIG. 11 shows a schematic cross-section view (SEC A-A) of the first example of a multi-zone IOL (MZ-IOL) previously shown in FIG. 10 according to the present invention. In this example, the MZ-IOL 30 comprises three adajacent radial zones: a central radial zone, A; a first (intermediate) annular zone, B; and a second (outermost) Annular Zone, C. These three radial zones (A, B, C) correspond uniquely to three different angles of incidence (alpha) of the aberrometer probe beam 16 relative to the optical axis 19 of the patent's eye (see FIG. 8 for definitions). FIG. 1 shows an example of an first aberrometer setup where the probe beam angle, alpha, =0 degrees, meaning that the probe beam 16 is parallel to, and coincides with, the optical axis 19 of the patient's eye. FIG. 8 shows an example of an second aberrometer setup where the angle, alpha=−20 degrees; meaning that the probe beam 16 is off-axis to (i.e., rotated down or to the side) relative to the optical axis 19 of the patient's eye. This setup in FIG. 8 corresponds, for example, to the 1st (intermediate) annular zone, B. A third setup (such as shown in FIG. 8 or 9) is not shown for brevity, but would be very similar to FIG. 8 or 9, and would have an even larger off-axis refraction angle, for example, alpha=−40 degrees, which corresponds to the $2^{nd}$ (outermost) annual zone, C. The central radial zone, A, has a radial extent=$R_1$. The $1^{st}$ annular zone, B, has a radial extent from R1 to $R_2$. Finally, the 2nd annular zone, C, has a radial extent from $R_2$ to $R_3$. The 3 different Zones represent regions of the MZ-IOL 30 where the shape of each zone has been physically modified to correct for both on-axis (Zone A), and off-axis wavefont aberration measurements (Zones B and C). A person of ordinary skill in the art will recognize that additional zones beyond three could be used, in order to improve the accuracy of the proposed vision improvement method.

The customized IOL can also comprise one or more toric fiducial marks that guide implantation of the IOL relative to a patient's axis of astigmatism.

The optical system of claim 1, wherein an off-axis angle of incidence (alpha) of an iris imaging path of the optical aberrometer is adjustable; and can be different (or can be the same) as an angle of an optical axis of the patient's eye ranging from 0 degrees up to +/−45 degrees, wherein aberrometer measurements are made of aberrations of the patient's eye at one or more off-axis angles.

In another embodiment, an uncorrected light-adjustable-lens (LAL) is first implanted and aligned in the patient's eye, followed by adjusting in-situ an shape and a refractive power of the LAL by applying an ultraviolet (UV) light delivery source to create an in-situ IOL customized by photo-polymerization of the IOL. This variation has been described in U.S. Pat. No. 10,166,731 to Grubbs and Sandstedt, which is incorporated herein by reference.

We claim:

1. An optical system for correcting a vision of a patient's eye, comprising:
    optical aberrometer means for measuring wavefront aberrations of a patient's eye and for displaying said measured aberrations across the eye;
    computational software means for designing a wavefront-customized correction profile that modifies a shape of an Intra Ocular Lens (IOL) by correcting for said measured aberrations;
    manufacturing means for creating a customized IOL with the wavefront-customized correction profile; and
    surgical means for implanting the customized IOL in the patient's eye;
    wherein the optical aberrometer comprises solenoid means for switching between a TSA optic, a dark field mask, a wavelength multiplexer mask, and a Spatial Light Modulator along an imaging path.

2. The optical system of claim 1, wherein the optical aberrometer comprises a motor for rotating a disk that repeatedly modulates light travelling down an optical path.

3. The optical system of claim 1, wherein the optical aberrometer comprises a wavelength multiplexed mask (WMM) that has a clear central aperature surrounded by an annular region; wherein the WMM blocks one selected wavelength of illumination light and passes a different wavelength.

4. The optical system of claim 1, wherein the optical aberrometer comprises a first illumination LED Source, a second illumination LED Source; and camera frame switching means for alternatively switching on/off alternate sequential frames of an iris camera using software control means.

5. The optical system of claim 1, wherein the optical aberrometer comprises location means for locating a XYZ location of a central aperture or other fiducial mark in an IOL; wherein said location means is selected from the group consisting of a split-prism range finder, OCT system, stereo cameras, and one or more bi-cell detectors, or combinations thereof.

6. The optical system of claim 1, wherein the customized IOL comprises one or more fiducial marks that comprise diffractive structures comprising regularly spaced apart holes, pits, or lines that scatter light preferentially more strongly at certain incident angles and color combinations; wherein a color camera can effectively "see" distance as color variations across a diffractively-coded image.

7. The optical system of claim 1, wherein the customized IOL comprises one or more toric fiducial marks that guide implantation of the IOL relative to a patient's axis of astigmatism.

8. The optical system of claim 1, wherein the IOL is a pseudophakic IOL, or a phakic IOL, or a Light-Adjustable-Lens (LAL).

* * * * *